United States Patent
Brines et al.

(10) Patent No.: US 7,384,625 B2
(45) Date of Patent: *Jun. 10, 2008

(54) METHOD AND COMPOSITION FOR REJUVENATING HAIR, NAILS, TISSUES, CELLS AND ORGANS BY EX-VIVO OR IMMERSIVE TREATMENT

(75) Inventors: Michael L. Brines, Woodbridge, CT (US); Anthony Cerami, Croton-On-Hudson, NY (US)

(73) Assignee: Farington Pharmaceuticals, LLC, Ossining, NY (US)

( * ) Notice: Subject to any disclaimer, the term of this patent is extended or adjusted under 35 U.S.C. 154(b) by 635 days.

This patent is subject to a terminal disclaimer.

(21) Appl. No.: 10/392,450

(22) Filed: Mar. 18, 2003

(65) Prior Publication Data

US 2003/0185776 A1    Oct. 2, 2003

Related U.S. Application Data

(63) Continuation of application No. 10/055,252, filed on Jan. 22, 2002, now Pat. No. 6,713,050.

(60) Provisional application No. 60/263,300, filed on Jan. 22, 2001.

(51) Int. Cl.
- *A61K 8/00* (2006.01)
- *A61K 8/18* (2006.01)
- *A61K 31/425* (2006.01)
- *A61Q 3/00* (2006.01)
- *A01N 43/78* (2006.01)
- *C07D 277/60* (2006.01)
- *C07D 277/62* (2006.01)

(52) U.S. Cl. .................. 424/61; 514/365; 514/367; 548/152

(58) Field of Classification Search .................. 424/61; 514/365, 367, 369, 370, 423; 548/152
See application file for complete search history.

(56) References Cited

U.S. PATENT DOCUMENTS 5,656,261 A * 8/1997 Cerami et al. .................. 424/53
5,853,703 A * 12/1998 Cerami et al. .................. 424/53
6,007,865 A    12/1999 Cerami et al.
6,121,300 A    9/2000 Cerami et al.
6,777,557 B2 * 8/2004 Ulrich et al. ................ 548/150
2002/0188015 A1 * 12/2002 Ulrich et al. ................ 514/365

OTHER PUBLICATIONS

Ulrich, P & Cerami, A, Protein Glycation, Diabetes, and Aging, Adv. Hormone Research, 1-21, 2001.

Valentin et al., "Donor treatment with mycophenolate mofetil," Transplantation, 69(3):344-350. 2/200.

* cited by examiner

*Primary Examiner*—Sreeni Padmanabhan
*Assistant Examiner*—Umamaheswari Ramachandran
(74) *Attorney, Agent, or Firm*—Frederick J. Hamble

(57) ABSTRACT

A method and composition for the treatment of hair, nail, ex-vivo organ, ex-vivo cell or ex-vivo tissue to improve the biomechanical and diffusional characteristics comprising an effective amount of a compound selected from the group consisting of compounds of the formula (I):

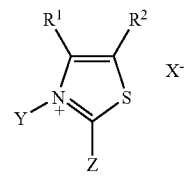

or the formula (II):

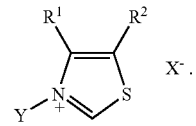

9 Claims, 2 Drawing Sheets

METHOD AND COMPOSITION FOR REJUVENATING HAIR, NAILS, TISSUES, CELLS AND ORGANS BY EX-VIVO OR IMMERSIVE TREATMENT

CROSS-REFERENCE TO RELATED APPLICATIONS

This application is a continuation, under 35 U.S.C. § 120, of U.S. patent application Ser. No. 10/055,252, filed Jan. 22, 2002 now U.S. Pat. No. 6,713,050, which claims the benefit under 35 U.S.C. § 119(e) of U.S. Provisional Application Ser. No. 60/263,300, filed Jan. 22, 2001.

BACKGROUND OF THE INVENTION

The present invention generally relates to the aging or damage of hair, nails, tissues, organs and cells and, more particularly, to the rejuvenation of hair, nails, tissues, cells, and organs by improving the deformability and diffusion coefficient of hair, nails, tissues, cells, and organs in humans and animals (including companion animals and live stock).

Various changes in the biomechanical and other functional properties of hair may occur with aging and diseases. Undesirable changes may include deterioration in manageability, including decreased stability and brittle hair. Typically, these detrimental changes may be due to: (a) physically or chemically damaged hair; (b) physiologically aged hair; and/or (c) diseased hair (e.g. hair of diabetics). Hair may be physically damaged from the normal grooming process of shampooing, combing, drying (e.g. hot air blow drying), and/or brushing. In addition to this physical damage of hair, hair may also be damaged by chemical action such as by exposure to sunlight and contact with water containing chemically reactive agents such as oxidizers (e.g bleaching and/or dyeing of hair). Also, the repeated use of permanent waving compositions on the hair fibers may cause damage to the hair especially if not used according to directions. Bleached hair is often characterized as being dry, brittle, and overly coarse. Finally, with the aging process, hair may become dry, brittle and overly coarse.

For nails, deterioration in the biomechanical and other functional properties may also result in undesirable nail problems. Conventionally, the term "nail" has meant the horny cutaneous plate on the dorsal surface of the distal end of a finger or toe, or the corresponding appendages in animals. Specifically, in humans, the hardness and strength of the nails is particularly important not only for the beauty of their appearance, but for the well-being of the individual. Embrittlement of the nails is normally associated with aging. However, various activities also expose nails to a number of materials which may adversely affect the nail's biomechanical and other functional properties. For example, occupational exposure to extensive or constant wetting of the hands with soaps, detergents, solvents, chemical hair waving and coloring lotions, and insults from deliberate cosmetic applications, such as manicuring, or any like products can lead to drying, brittleness, cracking, laminating, splitting, ridging and similar damage. Additionally, certain diseases may also lead to nail embrittlement or associated disfigurement owing to weakening of nail hardness and strength. Moreover, the appearance of fingernails and toenails of humans are frequently enhanced with decorative nail-care cosmetics, such as nail polishes, nail polish removers, nail polish bases, alkaline cuticle removers and the like. Overuse of these products can alter the nail, causing it to weaken, soften, split and break.

With respect to tissues, cells and organs, transplantation of these materials has become a routine means of treating certain diseases and other conditions. Transplantation requires a ready source of organs, such as kidney, pancreas, liver, heart, etc., from living persons or cadavers. Conventionally, most vital organs, cells and tissues, which are used for transplantation, are obtained from heart beating cadavers and preserved for variable periods of time prior to their transplantation. However, preservation methods merely attempt to maintain the present condition of the organ, cell or tissue. For this reason, the majority of organs, cells and tissues that are used for transplantation presently come from younger individuals who typically have tissues, cells and organs that have not been detrimentally affected by age or disease.

In contrast, because of the aging process or disease, older individuals have a deterioration in the biomechanical (e.g. deformability) and other functional properties of their cells, tissues and organs. For this reason, decreased deformability is associated with impaired tissue or organ functionality in itself, as optimal biomechanical function is demonstrated at deformability levels measured in young individuals and diminishes with progressively decreasing levels of deformability. Thus, at the present time, older individuals typically can not be candidates for organ, tissue or cell donation because preservation solutions merely attempt to preserve the present condition of the organ, cell or tissue.

Conventionally, two typical methods of preserving organs, cells and tissues for transplantation are continuous pulsatile perfusion and simple hypothermic storage in a preservation solution. In pulsatile perfusion, the organ is subjected to pulsatile flow of a perfusate under hypothermic conditions such that the organ membranes receive sufficient oxygenation. Typically, the perfusate contains albumin and lipids. With simple hypothermic storage, organs are removed from a cadaver donor and rapidly cooled. Rapid cooling is achieved by external cooling and by perfusion with a preservation solution to lower the internal temperature of the organ. The organ is then stored immersed in the preservation solution at temperatures of about 0°-4° C. Two conventional glucose preservation flush solutions are the Collins (G. M. Collins, The Lancet, 1969, 1219-1222) and the Euro-Collins (J. P. Squifflet et al, Transplant. Proc., 1981, 13:693-696) solutions. These solutions resemble intracellular fluid and contain glucose as an osmotic agent. Despite their widespread use, the Collins and Euro-Collins preservation solutions do not typically provide adequate preservation for storage times greater than about 48 hours. For example, kidneys stored in Collins solution for 24 hours may exhibit considerable damage to the nephrons. This damage included degradation of cells lining the proximal tubules, extensive swelling and rupturing of cells lining the ascending distal tubules, degeneration of glomerular epithelial and endothelial cells and accumulation of flocculent cytoplasmic debris in the capsular spaces of Bowman. (P. M. Andrews et al, Lab. Invest., 1982, 46:100-120). In addition to glucose flush solutions, high osmolality preservation solutions have been prepared using raffinose and lactobionate as in the UW preservation solution (R. J. Ploeg et al, Transplant. Proc., 1988, 20 (suppl 1) 1:935-938), mannitol in the Sacks solution (S. A. Sacks, The Lancet, 1973, 1:1024-1028), sucrose in the Transplantation, 1989, 47:767-771) and the histidine buffered HTK solution of Bretschneider (N. M. Kallerhoff et al, Transplantation, 1985, 39:485-489). Other examples are solutions that contain synthetic hydroxyethyl starch (HES) as an osmotic colloid.

SUMMARY OF THE INVENTION

In accordance with the present invention, a novel method and composition are disclosed for the "rejuvenation" of hair, nails, tissues, cells and organs by ex-vivo treatment. In particular, the composition comprises compounds for the ex-vivo treatment of hair, nails, tissues, cells and organs to improve the biomechanical and other functional properties of hair, nails, tissues, cells and organs. More particularly, for hair and nails, the composition and method of the present invention comprises compounds for rejuvenating: (a) damaged hair or nails; (b) physiologically aged hair or nails; and/or (c) diseased hair or nails (e.g. diabetes). For tissues, cells and organs, the composition and method of the present invention comprises compounds for rejuvenating tissues, cells and organs by improving the deformability and/or diffusion coefficient of tissues, cells and organs from a state of decreased deformability and impaired diffusional characteristics, as typically observed in cells, tissues or organs of older individuals, to a state of increased deformability and improved diffusional characteristics, as commonly seen in cells, tissues and organs of healthy and young individuals (i.e 20 years old).

Decreased deformability is associated with impaired tissue or organ functionality in itself, as optimal biomechanical function is demonstrated at deformability levels measured in young individuals and diminishes progressively with age. It is believed that the aging process, in addition to modifying the deformability, also induces additional specific impairments in the functionality of cells, tissues and/or organs that are not directly related to deformability. It is further believed that this impairment in functionality is related to an altered diffusion coefficient of molecules across intracellular and extracellular spaces. The altered ability of molecules to traverse intra- and extracellular spaces may affect signaling functions of hormones and cytokines, transportation of oxygen and nutrients from the vascular space to the cell, and cellular metabolism.

Commonly used methods to determine deformability include ultrasonographic techniques and the measurement of volume-pressure and stress-strain relationships. Commonly used methods to measure the diffusion coefficient of molecules across intracellular and extracellular spaces include the determination of the reaction time of biomolecular feed-back mechanisms based on the diffusion of molecules across a cellular, tissue and/or organ space to reach a target response element and the direct measurement of the diffusion rate of certain molecules across biological spaces. Examples of methods to determine the biomolecular feed-back mechanisms include, but are not limited to, the following: (a) hypothalamic-pituitary axis: growth hormone, ACTH, TSH, or prolactin; (b) pituitary-adrenal axis: cortisol; (c) pituitary-thyroid axis: thyroxin; and (d) pituitary-gonadal axis: sex hormones, LH, and FSH. Examples of methods to determine the diffusion rate of certain molecules across biological spaces include, but are not limited to, the following: arterio-alveolar oxygen and carbon dioxide gradients; insulin resistance; and arterio-venous oxygen gradient (e.g., heart, muscle).

In particular, the compositions comprise compounds for the ex-vivo treatment of hair, nails, organs, cells and tissues to rejuvenate them by changing deformability and increase the tissue diffusion coefficient. This treatment is accomplished by bathing or perfusing the biological material outside of the body. The compounds are members of the class of compounds known as thiazoliums.

In one embodiment, the compositions comprise thiazolium compounds having the following structural formula (I):

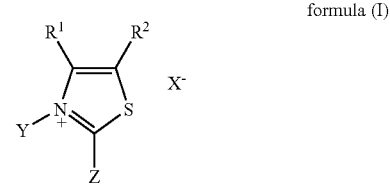

formula (I)

wherein $R^1$ and $R^2$ are independently selected from the group consisting of hydrogen, hydroxy(lower alkyl), lower acyloxy(lower alkyl), lower alkyl, lower alkenyl, or $R^1$ and $R^2$ together with their ring carbons may be an aromatic fused, ring, optionally substituted by one or more amino, halo or alkylenedioxy groups;

Z is hydrogen or an amino group;

Y is amino, a group of the formula —CH$_2$C(=O)—R wherein R is a lower alkyl, alkoxy, hydroxy, amino or aryl group; said aryl group optionally substituted by one or more lower alkyl, lower alkoxy, halo, dialkylamino, hydroxy, nitro or alkylenedioxy groups;

or a group of the formula —CH$_2$R' wherein R' is hydrogen, or a lower alkyl, lower alkynyl, or aryl group;

or a group of the formula —CH$_2$C(=O)—N(R")R'"

wherein (a) R" is hydrogen and R'" is a lower alkyl group, optionally substituted by a $C_6$-$C_{10}$ aryl group, or a $C_6$-$C_{10}$ aryl group, said aryl groups optionally substituted by one or more lower alkyl, halo, or (lower alkoxyl)carbonyl groups; or (b) R" and R'" are both lower alkyl groups;

X is a halide, tosylate, methanesulfonate, mesitylenesulfonate ion, or other pharmaceutically acceptable anion and mixtures thereof, and a carrier therefor.

In another embodiment, the composition comprises compounds having the following structural formula (II):

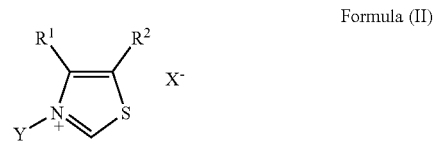

Formula (II)

wherein $R^1$ and $R^2$ are independently selected from the group consisting of hydrogen and an alkyl group optionally substituted by a hydroxy group;

Y is a group of the formula —CH$_2$C(=O)R wherein R is a heterocyclic group other than alkylenedioxyaryl containing 4-10 ring members and 1-3 heteroatoms selected from the group consisting of oxygen, nitrogen and sulfur; said heterocyclic group optionally substituted by one or more substituents selected from the group consisting of alkyl, oxo, alkoxycarbonylalkyl, aryl, and aralkyl groups; and said one or more substituents optionally substituted by one or more alkyl or alkoxy groups;

or a group of the formula —CH$_2$C(=O)—NHR' wherein R' is a heterocyclic group containing 4-10 ring members and 1-3 heteroatoms selected from the group consisting of oxygen, nitrogen, and sulfur; said heterocyclic group optionally substituted by one or more alkoxycarbonylalkyl groups;

and X is a halide, tosylate, methanesulfonate or mesitylenesulfonate ion, or other pharmaceutically acceptable anion.

The present invention also relates to a method for treating hair and nails and for the ex-vivo rejuvenation of organs, cells and tissues by organs, cells or tissues with a sufficient amount of one or more of the compounds of the present invention, or a composition containing a sufficient amount to achieve the desired result.

DETAILED DESCRIPTION OF THE INVENTION

Figure 1:
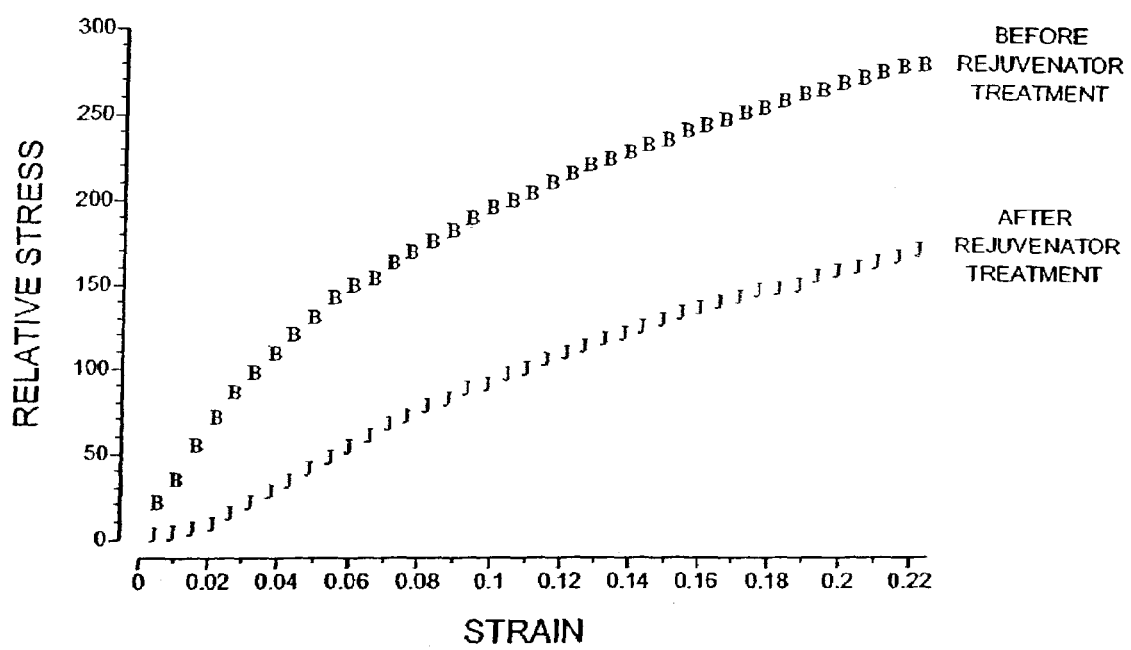
FIG. 1 shows that a composition of the present invention, 3-(2-phenyl-2-oxoethyl)-4,5-dimethyltbiazolium chloride, decreases the stiffness of hair after treatment.

A method and composition are disclosed for the "rejuvenation" of hair, nails, tissues, cells and organs by ex-vivo treatment. In particular, the composition comprises compounds for ex-vivo treating hair, nails, tissues, cells and organs to improve the biomechanical and other functional properties of hair, nails, tissues, cells and organs. More particularly, for hair and nails, the composition and method of the present invention comprises compounds for rejuvenating: (a) damaged hair or nails; (b) physiologically aged hair or nails; and/or (c) diseased hair or nails (e.g. diabetes). For tissues, cells and organs, the composition and method of the present invention comprise compounds for rejuvenating tissues, cells and organs by improving the deformability and/or diffusion coefficient of tissues, cells and organs from a state of decreased deformability and impaired diffusional characteristics, as typically observed in cells, tissues or organs of older individuals, to a state of increased deformability and improved diffusional characteristics, as commonly seen in cells, tissues and organs of healthy and young individuals (i.e 20 years old).

In one embodiment, the invention relates to a composition for the ex-vivo treatment of hair, nails, organs, cells and tissues to improve the biomechanical and functional properties comprising one or more agents comprising of thiazole compounds having the structural formula (I):

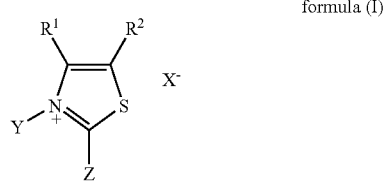

formula (I)

wherein $R^1$ and $R^2$ are independently selected from the group consisting of hydrogen, hydroxy(lower alkyl), lower acyloxy(lower alkyl), lower alkyl, lower alkenyl, or $R^1$ and $R^2$ together with their ring carbons may be an aromatic fused, ring, optionally substituted by one or more amino, halo or alkylenedioxy groups;
Z is hydrogen or an amino group;
Y is amino, a group of the formula —CH$_2$C(=O)—R wherein R is a lower alkyl, alkoxy, hydroxy, amino or aryl group; said aryl group optionally substituted by one or more lower alkyl, lower alkoxy, halo, dialkylamino, hydroxy, nitro or alkylenedioxy groups;
or a group of the formula —CH$_2$ R' wherein R' is hydrogen, or a lower alkyl, lower alkynyl, or aryl group;
or a group of the formula —CH$_2$C(=O)—N(R")R'" wherein (a) R" is hydrogen and R'" is a lower alkyl group, optionally substituted by a C$_6$-C$_{10}$ aryl group, or a C$_6$-C$_{10}$ aryl group, said aryl groups optionally substituted by one or more lower alkyl, halo, or (lower alkoxy)carbonyl groups; or (b) R' and R'" are both lower alkyl groups;
X is a halide, tosylate, methanesulfonate, mesitylenesulfonate, or other pharmacologically acceptable anion and mixtures thereof, and a carrier therefor.

The lower alkyl groups referred to above contain 1-6 carbon atoms and include methyl, ethyl, propyl, butyl, pentyl, hexyl, and the corresponding branched-chain isomers thereof. The lower alkenyl groups and lower alkynyl groups independently contain from 2 to 6 carbon atoms. Similarly, the lower alkoxy groups contain from 1 to 6 carbon atoms, and include methoxy, ethoxy, propoxy, butoxy, pentoxy, and hexoxy, and the corresponding branched-chain isomers thereof. These groups are optionally substituted by one or more halo, hydroxy, amino or lower alkylamino groups.

The lower acyloxy(lower alkyl) groups encompassed by the above formula include those wherein the acyloxy portion contains from 2 to 6 carbon atoms and the lower alkyl portion contains from 1 to 6 carbon atoms. Typical acyloxy portions are those such as acetoxy or ethanoyloxy, propanoyloxy, butanoyloxy, pentanoyloxy, hexanoyloxy, and the corresponding branched chain isomers thereof. Typical lower alkyl portions are as described hereinabove. The aryl groups encompassed by the above formula are those containing 6-10 carbon atoms, such as phenyl and lower alkyl substituted-phenyl, e.g., tolyl and xylyl, and are optionally substituted by 1-2 halo, hydroxy, lower alkoxy or di(lower alkyl)amino groups. Preferred aryl groups are phenyl, methoxyphenyl and 4-bromophenyl groups. The halo atoms in the above formula may be fluoro, chloro, bromo or iodo.

For the purposes of this invention, the compounds of formula (I) are formed as biologically and pharmaceutically acceptable salts. Useful salt forms are the halides, particularly the bromide and chloride, tosylate, methanesulfonate, and mesitylenesulfonate salts. Other related salts can be formed using similarly non-toxic, and biologically and pharmaceutically acceptable anions.

Representative compounds of the present invention are:
3-aminothiazolium mesitylenesulfonate;
3-amino-4,5-dimethylaminothiazolium mesitylenesulfonate;
2,3-diaminothiazolium mesitylenesulfonate;
3-(2-methoxy-2-oxoethyl)thiazolium bromide;
3-(2-methoxy-2-oxoethyl)-4,5-dimethylthiazolium bromide;
3-(2-methoxy-2-oxoethyl)-4-methylthiazolium bromide;
3-(2-phenyl-2-oxoethyl)-4-methylthiazolium bromide;
3-(2-phenyl-2-oxoethyl)-4,5-dimethylthiazolium bromide;
3-(2-phenyl-2-oxoethyl)-4,5-dimethylthiazolium chloride;
3-amino-4-methylthiazolium mesitylenesulfonate;
3-(2-methoxy-2-oxoethyl)-5-methylthiazolium bromide;
3-(3-(2-phenyl-2-oxoethyl)-5-methylthiazolium bromide;
3-[2-(4-bromophenyl)-2-oxoethyl]thiazolium bromide;
3-[2-(4-bromophenyl)-2-oxoethyl]-4-methylthiazolium bromide;

3-[2-(4-bromophenyl)-2-oxoethyl]-5-methylthiazolium bromide;
3-[2-(4-bromophenyl)-2-oxoethyl]-4,5-dimethylthiazolium bromide;
3-(2-methoxy-2-oxoethyl)-4-methyl-5-(2-hydroxyethyl) thiazolium bromide;
3-(2-phenyl-2-oxoethyl)-4-methyl-5-(2-hydroxyethyl)thiazolium bromide;
3-[2-(4-bromophenyl)-2-oxoethyl]-4-methyl-5-(2-hydroxyethyl)thiazolium bromide;
3,4-dimethyl-5-(2-hydroxyethyl)thiazolium iodide;
3-ethyl-5-(2-hydroxyethyl)-4-methylthiazolium bromide;
3-benzyl-5-(2-hydroxyethyl)-4-methylthiazolium chloride;
3-(2-methoxy-2-oxoethyl)benzothiazolium bromide;
3-(2-phenyl-2-oxoethyl)benzothiazolium bromide;
3-[2-(4'-bromophenyl)-2-oxoethyl]benzothiazolium bromide;
3-(carboxymethyl)benzothiazolium bromide;
2,3-diaminobenzothiazolium mesitylenesulfonate;
3-(2-amino-2-oxoethyl)thiazolium bromide;
3-(2-amino-2-oxoethyl)-4-methylthiazolium bromide;
3-(2-amino-2-oxoethyl)-5-methylthiazolium bromide;
3-(2-amino-2-oxoethyl)4,5-dimethylthiazolium bromide;
3-(2-amino-2-oxoethyl)benzothiazolium bromide;
3-(2-amino-2-oxoethyl)-4-methyl-5-(2-hydroxyethyl)thiazolium bromide;
3-amino-5-(2-hydroxyethyl)-4-methylthiazolium mesitylenesulfonate;
3-(2-methyl-2-oxoethyl)thiazolium chloride;
3-amino-4-methyl-5-(2-acetoxyethyl)thiazolium mesitylenesulfonate;
3-(2-phenyl-2-oxoethyl)thiazolium bromide;
3-(2-methoxy-2-oxoethyl)-4-methyl-5-(2-acetoxyethyl) thiazolium bromide;
3-(2-amino-2-oxoethyl)-4-methyl-5-(2-acetoxyethyl)thiazolium bromide;
2-amino-3-(2-methoxy-2-oxoethyl)thiazolium bromide;
2-amino-3-(2-methoxy-2-oxoethyl)benzothiazolium bromide;
2-amino-3-(2-amino-2-oxoethyl)thiazolium bromide;
2-amino-3-(2-amino-2-oxoethyl)benzothiazolium bromide;
3-[2-(4-methoxyphenyl)-2-oxoethyl]thiazolium bromide;
3-[2-(2,4-dimethoxyphenyl)-2-oxoethyl]thiazolium bromide;
3-[2-(4-fluorophenyl)-2-oxoethyl]thiazolium bromide;
3-[2-(2,4-difluorophenyl)-2-oxoethyl]thiazolium bromide;
3-[2-(4-diethylaminophenyl)-2-oxoethyl]thiazolium bromide;
3-propargylthiazolium bromide;
3-propargyl-4-methylthiazolium bromide;
3-propargyl-5-methylthiazolium bromide;
3-propargyl-4,5-dimethylthiazolium bromide;
3-propargyl-4-methyl-5-(2-hydroxyethyl)thiazolium bromide.
(2-(3-methoxyphenyl)-2-oxoethyl)thiazolium bromide;
3-(2-(3-methoxyphenyl)-2-oxoethyl)-4 methyl-5-(2-hydroxyethyl)thiazolium bromide;
3-(2-(3-methoxyphenyl)-2-oxoethyl)benzothiazolium bromide;
2,3-diamino-4-chlorobenzothiazolium mesitylenesulfonate;
2,3-diamino-4-methylthiazolium mesitylenesulfonate;
3-amino-4-methyl-5-vinylthiazolium mesitylenesulfonate;
2,3-diamino-6-chlorobenzothiazolium mesitylenesulfonate;
2,6-diaminobenzothiazole dihydrochloride;
2,6-diamino-3-(2-(4-methoxyphenyl)-2-oxoethyl)benzothiazolium bromide;
2,6-diamino-3-(2-(3-methoxyphenyl)-2-oxoethyl)benzothiazolium bromide;
2,6-diamino-3-(2-(4-diethylaminophenyl)-2-oxoethyl)benzothiazolium bromide;
2,6-diamino-3-(2-(4-bromophenyl)-2-oxoethyl)benzothiazolium bromide;
2,6-diamino-3-(2-(2-phenyl-2-oxoethyl)benzothiazolium bromide;
2,6-diamino-3-(2-(4-fluorophenyl-2-oxoethyl)benzothiazolium bromide;
3-acetamido-4-methyl-5-(2-acetoxyethyl)thiazolium mesitylenesulfonate;
2,3-diamino-5-methylthiazolium mesitylenesulfonate;
3-(2-(2-naphthyl)-2-oxoethyl)-4-methyl-5-(2-hydroxyethyl) thiazolium bromide;
3 -(2-(3,5-di-tert-butyl-4-hydroxyphenyl)-2 -oxoethyl)-4-methyl-5 -(2-hydroxyethyl)thiazolium bromide;
3-(2-(2-(2,6-dichlorophenyl)ethylamino)-2-oxoethyl)-4-methyl-5-(2-hydroxyethyl)thiazolium bromide;
3-(2-dibutylamino-2-oxoethyl)-4-methyl-5-(2-hydroxyethyl)-thiazolium bromide;
3-(2-(4-(ethoxycarbonyl)anilino)-2-oxoethyl)-4-methyl-5-(2-hydroxyethyl)thiazolium bromide;
3-(2-(2,6-diisopropylanilino)-2-oxoethyl)-4-methyl-5-(2-hydroxyethyl)thiazolium bromide;
3-amino-4-methyl-5-(2-(2,6-dichlorobenzyloxy)ethyl) thioazolium mesitylenesulfonate;
3-(2-(4-carbomethoxy-3-hydroxyanilino)-2-oxoethyl)-4-methyl-5-(2-hydroxyethyl)thiazolium bromide;
2,3-diamino-4,5-dimethylthiazolium mesitylene sulfonate;
2,3-diamino-4-methyl-5-(2-hydroxyethyl)thiazolium mesitylene sulfonate;
2,3-diamino-5-(3,4-trimethylenedioxy phenyl)thiazolium mesitylene sulfonate;
3-(2-(1,4-benzodioxan-6-yl)-2-oxoethyl)-4-methyl-5-(2-hydroxyethyl)thiazolium bromide;
3-(2-(3,4-trimethylenedioxyphenyl)-2-oxoethyl)-4-methyl-5-(2-hydroxyethyl)thiazolium bromide;
3-(2-(1,4-benzodioxan-6-yl)-2-oxoethyl)thiazolium bromide;
3-(2-(3,4-trimethylenedioxyphenyl)-2-oxoethyl)thiazolium bromide;
3-(2-(3,5-di-tert-butyl-4-hydroxyphenyl)-2-oxoethyl)-thiazolium bromide;
3-(2-(3,5-di-tert-butyl-4-hydroxyphenyl)-2-oxoethyl)-4-methylthiazolium bromide;
3-(2-(3,5-di-tert-butyl-4-hydroxyphenyl)-2-oxoethyl)-5-methylthiazolium bromide;
3-(2-(3,5-di-tert-butyl-4-hydroxyphenyl)-2-oxoethyl)-4,5-dimethylthiazolium bromide;
3-(2-(3,5-di-tert-butyl-4-hydroxyphenyl)-2-oxoethyl)benzothiazolium bromide;
3-(2-(4-n-pentylphenyl)-2-oxoethyl)thiazolium bromide;
3-(2-(4-n-pentylphenyl)-2-oxoethyl)-4-methyl-5-(2-hydroxyethyl)thiazolium bromide;
3-(2-4-diethylaminophenyl)-2-oxoethyl)-4-methyl-5-(2-hydroxyethyl)thiazolium bromide;
3-(2-phenyl-2-oxoethyl)-4-methyl-5-vinylthiazolium bromide;
3-(2-(3,5-di-tert-butyl-4-hydroxyphenyl)-2-oxoethyl)-4-methyl-5-vinylthiazolium bromide;
3-(2-tert-butyl-2-oxoethyl)thiazolium bromide;
3-(2-tert-butyl-2-oxoethyl)-4-methyl-5-(2-hydroxyethyl) thiazolium bromide;
3-(3-methoxybenzyl)-4-methyl-5-(2-hydroxyethyl)thiazolium chloride;

3-(2,6-dichlorobenzyl)-4-methyl-5-(2-hydroxyethyl)thiazolium chloride;

3-(2-nitrobenzyl)-4-methyl-5-(2-hydroxyethyl)thiazolium bromide;

3-(2-(4-chlorophenyl)-2-oxoethyl)thiazolium bromide;

3-(2-(4-chlorophenyl)-2-oxoethyl)-4-methyl-5-(2-hydroxyethyl)thiazolium bromide; and 3-(2-(4-methoxyphenyl)-2-oxoethyl)-4-methyl-5-(2-hydroxyethyl)thiazolium bromide.

U.S. Pat. Nos. 5,656,261 and 6,007,865 disclose the compounds represented by Formula I, and their syntheses, which are hereby incorporated by reference herein.

In another embodiment, the compositions comprise thiazolium compounds having the following structural formula (II):

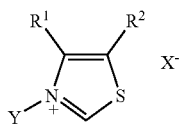

Formula (II)

wherein $R^1$ and $R^2$ are independently selected from the group consisting of hydrogen and an alkyl group optionally substituted by a hydroxy group; Y is a group of the formula —$CH_2C$(=O)R wherein R is a heterocyclic group containing 4-10 ring members and 1-3 heteroatoms selected from the group consisting of oxygen, nitrogen and sulfur; said heterocyclic group optionally substituted by one or more substituents selected from the group consisting of alkyl, oxo, alkoxycarbonylalkyl, aryl, and aralkyl groups; and said one or more substituents optionally substituted by one or more alkyl or alkoxy groups;

or a group of the formula —$CH_2C$(=O)—NHR' wherein R' is a heterocyclic group containing 4-10 ring members and 1-3 heteroatoms selected from the group consisting of oxygen, nitrogen, and sulfur; said heterocyclic group optionally substituted by one or more alkoxycarbonylalkyl groups;

and X is a halide, tosylate, methanesulfonate or mesitylenesulfonate ion or other pharmacologically acceptable anion.

The heterocyclic groups referred to herein include 4-8 membered rings having at least one and up to 3 heteroatoms, e.g. oxygen nitrogen, or sulfur, therein, and including various degrees of unsaturation. Representatives of such heterocyclic groups are those such as isoxazolyl, phenylisoxazolyl, furanyl, morpholino, thiomorpholino, pyrimidinyl, piperidino, homopiperidino, piperazino, methylpiperazino, hexamethyleneimino, tetrahydroquinolyl, pyridyl, methylpyridyl, imidazolyl, pyrrolidinyl, 2,6-dimethylmorpholino, 1,2,4-triazoylyl, thiazolyl, thienyl, thiazolinyl, methylthiazolyl, and the like. The heterocyclic groups of the present invention may be further substituted, for example, by an oxo group, to form, for example, a 2-oxo-tetrahydroquinolinyl group, or substituted by one or more alkyl, alkoxycarbonylalkyl, aryl, or aralkyl groups, and such substituents may be further substituted by one or more alkyl or alkoxy groups.

Examples of Y groups of the compounds of the present invention include, but are not limited to: 3-[2-(3-phenyl-5-isoxazolyl)-2-oxoethyl]; 3-(2-(4-morpholinyl)-2-oxoethyl); 3-[2-(2,6-dimethyl-4-morpholinyl)-2-oxoethyl];3-(2-(1-piperidinyl)-2-oxoethyl); 3-[2-(2-oxo-1,2,3,4-tetrahydro-6-quinolinyl)-2-oxoethyl]; 3-(2-(1-pyrrolidinyl)-2-oxoethyl; 3-[2-(3-methyl-2-thianaphthenyl)-2-oxoethyl]; 3-[2-(4-phenyl-1-piperazinyl)-2-oxoethyl; 3-(2-(2-thienyl)-2-oxoethyl); 3-(2-(2-thienyl)-2-oxoethyl); 3-(2-(4-thiomorpholinyl)-2-oxoethyl); 3-(2-(hexahydro-1-azepinyl)-2-oxoethyl), 3-[2-(4-[2-methoxyphenyl]-1-piperazinyl)-2-oxoethyl; 3-(2-(octahydro-1-azocinyl)-2-oxoethyl; 3-(2-(2-pyridinyl)-2-oxoethyl; 3-[2-(2-methyl-1-piperidinyl)-2-oxoethyl]; 3-[2-(2,6-dimethyl-1-piperidinyl)-2-oxoethyl; 3-[2-(4-benzyl-1-piperidinyl-2-oxoethyl]; and 3-[2-(4-benzyl-1-piperazinyl)-2-oxoethyl].

The alkyl groups referred to above contain one to about eighteen carbon atoms and include, for example, methyl, ethyl, propyl, butyl, pentyl, hexyl, octyl, decyl, dodecyl, and octadecyl, and the corresponding branched-chain isomers thereof. Lower alkyl groups, of one to about six carbon atoms, are preferred. The alkyl groups optionally substituted by hydroxy groups include alkyl groups as hereinbefore defined substituted with a hydroxy group at any position, such as but not limited to the following examples: hydroxymethyl, 1-hydroxyethyl, 2-hydroxyethyl, 1-hydroxypropyl, 2-hydroxypropyl, 3-hydroxypropyl, 6-hydroxyhexyl, and the like. Hydroxy-substituted lower alkyl groups as defined above are preferred. Similarly, the alkoxy groups contain from one to about eighteen carbon atoms, and include, for example, methoxy, ethoxy, propoxy, butoxy, pentoxy, hexoxy, decoxy, and octadecoxy, and the corresponding branched-chain isomers thereof. Lower alkoxy groups of one to about 6 carbons, are preferred. The alkoxycarbonylalkyl groups encompassed by the above formula include those wherein the alkoxy portion contain from one to about eighteen carbon atoms and the alkyl portion contains from 1 to about eighteen carbon atoms. Typical alkoxycarbonyl portions are those such as acetoxy or ethanoyloxy, propanoyloxy, butanoyloxy, pentanoyloxy, hexanoyloxy, decanoyloxy, and octadecanoyloxy, and the corresponding branched chain isomers thereof.

The aryl groups encompassed by the above formula are those containing 6-10 carbon atoms, such as naphthyl, phenyl and alkyl or alkoxy substituted-phenyl, e.g., toluyl and xylyl.

For the purposes of this invention, the compounds of the present invention are formed as biologically and pharmaceutically acceptable salts. Useful salt forms are the halides, particularly the bromide and chloride, tosylate, methanesulfonate, and mesitylenesulfonate salts. Other related salts can be formed using similarly non-toxic, and biologically and pharmaceutically acceptable anions. As described in the formula above, the heterocyclic group may be represented by the R group of the formula —$CH_2C$(=O)—R, or it may represent the R' group of the formula —$CH_2C$(=O)—NHR'.

Representative, non-limiting examples of compounds of the present invention are:

3-[2-(3-phenyl-5-isoxazolyl)-2-oxoethyl]thiazolium bromide;

3-[2-(3-phenyl-5-isoxazolyl)-2-oxoethyl]-4,5-dimethylthiazolium bromide;

3-[2-(3-phenyl-5-isoxazolyl)-2-oxoethyl]-4-methyl-5-(2-hydroxyethyl)thiazolium bromide;

3-[2-[4-(2-ethoxy-2-oxoethyl)-2-thiazolyl]amino-2-oxoethyl]-4,5-dimethylthiazolium chloride;

3-[2-(3-phenyl-5-isoxazolyl)-2-oxoethyl]-4-methyl-5-(6-hydroxyethyl)thiazolium bromide;

3-[2-(2,6-dimethyl-4-morpholinyl)-2-oxoethyl]-4,5-dimethylthiazolium bromide;

3-(2-(1-piperidinyl)-2-oxoethyl)-4,5-dimethylthiazolium bromide;
3-(2-(2-furanyl)-2-oxoethyl)-4,5-dimethylthiazolium bromide;
3-(2-(2-furanyl)-2-oxoethyl)-4-(2-hydroxypentyl)thiazolium bromide;
3-[2-(2-oxo-1,2,3,4-tetrahydro-6-quinolinyl)-2-oxoethyl]-4,5-dimethylthiazolium bromide;
3-(2-(1-pyrrolidinyl)-2-oxoethyl)-4,5-dimethyl-thiazolium bromide;
3-[2-(3-methyl-2-thianaphthenyl)-2-oxoethyl]-4,5-dimethylthiazolium bromide;
3-[2-(4-phenyl-1-piperazinyl)-2-oxoethyl]-4,5-dimethylthiazolium bromide;
3-(2-(2-thienyl)-2-oxoethyl)-4,5-dimethyl-thiazolium bromide;
3-(2-(2-thienyl)-2-oxoethyl)-4-methyl-5-hydroxyethylthiazolium bromide 3-(2-(4-thiomorpholinyl)-2-oxoethyl)-4,5-dimethylthiazolium bromide;
3-(2-(hexahydro-1-azepinyl)-2-oxoethyl)-4,5-dimethylthiazolium bromide;
3-[2-(4-[2-methoxyphenyl]-1-piperazinyl)-2-oxoethyl]-4,5-dimethylthiazolium chloride;
3-(2-(octahydro-1-azocinyl)-2-oxoethyl)-4,5-dimethyl-thiazolium bromide 3-(2-(2-pyridinyl)-2-oxoethyl)-4,5-dimethylthiazolium bromide;
3-[2-(2-methyl-1-piperidinyl)-2-oxoethyl]-4,5-dimethylthiazolium chloride;
3-[2-(2,6-dimethyl-1-piperidinyl)-2-oxoethyl]-4,5-dimethylthiazolium chloride;
3-[2-(4-benzyl-1-piperidinyl)-2-oxoethyl]-4,5-dimethylthiazolium chloride;
3-[2-(4-benzyl-1-piperazinyl)-2-oxoethyl]-4,5-dimethylthiazolium chloride;
3-[2-(3-phenyl-5-isoxazolyl)-2-oxoethyl]-4-octylthiazolium bromide;
3-(2-(4-morpholinyl)-2-oxoethyl)-4,5-dimethylthiazolium bromide;
3-[2-[4-(2-ethoxy-2-oxoethyl)-2-thiazolyl]amino-2-oxoethyl]-4,5-dipropylthiazolium chloride;
3-(2-(4-morpholinyl)-2-oxoethyl)-4,5-di(octadecyl)thiazolium bromide;
3-[2-(2,6-dimethyl-4-morpholinyl)-2-oxoethyl]-4,5-dipentylthiazolium bromide;
3-(2-(1-piperidinyl)-2-oxoethyl)-4,5-didodecylthiazolium bromide;
3-(2-(2-furanyl)-2-oxoethyl)-5-decylthiazolium bromide;
3-[2-(2-oxo-1,2,3,4-tetrahydro-6-quinolinyl)-2-oxoethyl]-4,5-dioctylthiazolium bromide;
3-(2-(1-pyrrolidiny)-2-oxoethyl)-4,5-diethylthiazolium bromide;
3-[2-(3-methyl-2-thianaphthenyl)-2-oxoethyl]-4,5-dipentylthiazolium bromide;
3-[2-(4-phenyl-1-piperazinyl)-2-oxoethyl]-thiazolium bromide;
3-(2-(2-thienyl)-2-oxoethyl)-thiazolium bromide;
3-(2-(2-thienyl)-2-oxoethyl)-4-methyl-5-(6-hydroxyhexyl)thiazolium bromide;
3-(2-(4-thiomorpholinyl)-2-oxoethyl)thiazolium bromide;
3-(2-(hexahydro-1-azepinyl)-2-oxoethyl)-4,5-dioctylthiazolium bromide;
3-(2-(octahydro-1-azocinyl)-2-oxoethyl)-4,5-didecylthiazolium bromide;
3-(2-(2-pyridinyl)-2-oxoethyl)-4,5-dioctylthiazolium bromide;
3-[2-(2-methyl-1-piperidinyl)-2-oxoethyl]-4,5-dipropylthiazolium chloride;
3-[2-(2,6-dimethyl-1-piperidinyl)-2-oxoethyl]-4-methylthiazolium chloride;
3-[2-(4-benzyl-1-piperidinyl)-2-oxoethyl]-5-methylthiazolium chloride;
3-[2-(4-benzyl-1-piperazinyl)-2-oxoethyl]-4-octylthiazolium chloride;

The compounds represented by Formula II are disclosed in U.S. Pat. No. 6,121,300. The syntheses of these compounds, discussed in U.S. Pat. No. 6,121,300, are hereby incorporated by reference herein. Pharmaceutical compositions may be prepared with a therapeutically effective quantity of the agents or compounds of the present invention and may include a pharmaceutically acceptable carrier, selected from known materials utilized for this purpose. Such compositions may be prepared in a variety of forms, depending on the method of administration. Also, various pharmaceutically acceptable addition salts of the compounds of the present invention may be utilized.

In a further embodiment, the present invention relates to methods for treating hair and nails and ex-vivo treatment of organs, cells and tissues that comprise contacting the targeted area with a composition of the present invention. In an embodiment, for topical application to hair or nails, a solution, a lotion or ointment may be formulated one or more with agents or compounds in a suitable vehicle such as water, ethanol, propylene glycol, perhaps including a carrier to aid in contacting the hair or nails. For example, a topical preparation could include up to about 10% of the compound of Formula I or II, or mixtures thereof. Other suitable forms for administration to other body tissues are also contemplated.

The agent or compound of Formula I or II is formulated in compositions in an amount effective to return the biomechanical and diffusional characteristics of the sample to the state of a healthy 20 year old. This amount will, of course, vary with the particular agent being utilized and the particular dosage form, but typically is in the range of 0.01% to 1.0%, by weight, of the particular formulation.

In one embodiment relating to the treatment of hair, the compounds discussed above may be combined with other components to form a composition that may be used to treat: (a) damaged hair; (b) physiologically aged hair; and (c) diseased hair (e.g. diabetes). The compositions of the present invention may be compounded and/or mixed with shampoo compositions containing, anionic, nonionic and cationic surfactants, as well as hair conditioning compositions. In yet another embodiment, the compositions of the present invention may be incorporated with conventional hair treating compositions such as bleaching compositions, hair dyeing compositions and/or hair relaxers.

In an embodiment that includes a hair treatment composition of the present invention, surface active agents may be used and include, but are not limited to, coconut oil fatty acids or oleic acid, alkali metal or ammonium or amine soaps, water-soluble lauryl sulfate salts, usually alkali metal, ammonium and ethanolamine, commonly diethanolamine or triethanolamine, salts; alkanolamine salts of linear $C_{12}$-$C_{15}$ alkyl benzene sulfonic acids; water-soluble polyethoxylauryl alcohol sulfate salts; linear alkyl benzene polyoxyethyl sulfonate salts; sulfated lauric acid monoglyceride salts; quaternary ammonium compounds such as cetyltrimethyl ammonium chloride; nonionic detergents such as octylphenoxypoly(ethyleneoxy)ethanol; and amphoteric detergents.

In a further embodiment, a shampoo composition of the present invention may include foam boosters or foam stabilizers. Such boosters include, but are not limited to, dialkylolamides of $C_8$-$C_{18}$ fatty acids, as, for instance, lauric or cocodiethanolamides which are represented by the formula R—CO—N—(CH$_2$—CH$_2$—OH)$_2$ where R—CO is a saturated fatty acid acyl radical of C$_8$-C$_{15}$ fatty acids, particularly lauric acid or myristic acid or mixtures of saturated fatty acids containing predominately from C$_{12}$ to C$_{14}$ fatty acids and commonly derived from coconut oil.

In one embodiment, the composition for treating hair may be adjusted to a pH from about 6 to about 9, more particularly from about 5.5 to about 7.5.

In a further embodiment, the composition for treating hair may include supplemental ingredients for particular purposes such as polymers, combing aids, etc.—liquids, gels, creams or dry powders.

In an embodiment relating to the treatment of nails, the compounds discussed above may be combined with conventional nail polish components to form a composition that may be used to treat: (a) damaged nails; (b) physiologically aged nails; and (c) diseased nails (e.g. diabetes). The nail polish compositions of the present invention may include various solvents, resins, FDA certified pigments, and pigment extenders. The following are illustrative examples of each of these components. For example, solvents may include n-butyl acetate (ester solvent), ethyl acetate (ester solvent), propylene glycol methyl ether acetate (ester solvent), isopropyl alcohol (oxygenated solvent), dipropylene glycol methyl ether (glycol ether solvent), naphtha/petroleum naphtha (aliphatic petroleum solvent) mineral spirits (aliphatic petroleum solvent). For example, resins may include acrylic resin (a polymer of acrylic-methacrylic acids and their esters), maleated-rosin (rosin-maleic adduct), nitrocellulose (soluble cellulose ester), pigment. In addition, FD&C colors and/or FDA certified pigments may be used. In a further embodiment, pigment extenders may be used such as magnesium silicate (Vantac 6H), silicone dioxide (amorphous silica), aluminum stearate, calcium carbonate, barium sulfate, aluminum silicate, calcium silicate and calcium sulfate.

In a further embodiment, the composition of the present invention may include antifungal agents such as miconazole nitrate, ketoconazole, itraconazole, fluconazole, econazole, terconazole, saperconazole, amorolfine, ciclopirox, oxiconazole, clotrimazole, terbinafine, naftifine, and other antifungal drugs that are available in a topical formulation. In addition, the formulation containing the antifungal drug may include an agent such as hydroxypropyl-alpha-cyclodextrin that enhances the water-solubility of the antifungal drug. The anti-fungal drugs are used in anti-fungally effective amounts. For example, anti-fungally effective amounts may be from about 0.5% to about 10%, by weight, and more particularly from about 1% to about 5%, by weight, of the formulation that is applied to the nail or surrounding dermal tissue.

In another embodiment, the present compositions may be applied in the area of tissue "rejuvenation". For purposes of the present invention, the terms "cells", "tissues" and "organs" may be used interchangeably as organs consist of tissue and tissue contain cells and extracellular material. The term "rejuvenation" means sufficiently improving the deformability and/or diffusion coefficient of cells, tissues and/or organs from a state of decreased deformability and impaired diffusional characteristics, as typically observed in cells, tissues or organs of older individuals, to a state of increased deformability and improved diffusional characteristics, as commonly seen in cells, tissues and organs of healthy and young individuals (e.g., 20 years old). One method of determining whether the cells, tissues or organs have been "rejuvenated" is whether, after treatment with the compositions of the present invention, the biomechanical and diffusional characteristics of the treated cells, tissues or organs have been changed by at least 20% toward the characteristics of a healthy 20 year old.

Decreased deformability is associated with impaired tissue or organ functionality in itself, as optimal biomechanical function is demonstrated at deformability levels measured in healthy and young individuals and diminishes with progressively decreasing levels of deformability. It is believed that the aging process, in addition to modifying the deformability, also induces additional specific impairments in the functionality of cells, tissues and/or organs that are not directly related to deformability. It is further believed that this impairment in functionality is related to an altered diffusion coefficient of molecules across intracellular and extracellular spaces. The decreased ability of molecules to traverse intra- and extracellular spaces may affect signaling functions of hormones and cytokines, transportation of oxygen and nutrients from the vascular space to the cell, and cellular metabolism.

Table 1 below is an illustrative list of various types of tissues, cells and organs that may be treated with the composition and method of the present invention. This list is merely illustrative and should not be construed as limiting the invention.

TABLE 1

| Cells | Tissues | Organs |
| --- | --- | --- |
| Beta cells of pancreas | Tendons | Heart |
| Cardiac myocytes | Ligaments | Lungs |
| Neurons | Bone | Kidneys |
| Macrophages | Vessels | Liver |
| Erythrocytes | Cardiac valves | Spleen |
| Leukocytes | Cornea | Adrenals |
| Fibrocytes | | Gonads |
| | | Skin |

For purposes of the present invention, "rejuvenation" may be measured by one or more of the techniques to measure deformability and/or other functionality of tissues, cells or organs. Commonly used methods to determine deformability include ultrasonographic techniques and the determination of volume-pressure and stress-strain relationships, but are not limited to these. Table 2 is an illustrative list of some of the currently available measures used for evaluating aspects of deformability: This list is merely illustrative and should not be construed as limiting the techniques that may be used to measure the deformability of tissues, cells or organs.

TABLE 2

| | Cells | Tissues | Organs |
| --- | --- | --- | --- |
| In vitro | Membrane deformability | Compliance Distensibility Impedance Tensile strength Wall tension Compressive strength Flexibility Torsion Elasticity Viscoelasticity Shear | Compliance Distensibility Impedance Wall tension Compressive strength Flexibility Torsion Elasticity Viscoelasticity Shear |
| In vivo | Membrane deformability | Compliance Distensibility Impedance Wall tension | Compliance Distensibility Impedance Wall tension |

TABLE 2-continued

| Cells | Tissues | Organs |
|---|---|---|
| | Flexibility | Flexibility |
| | Elasticity | Elasticity |
| | Viscoelasticity | Viscoelasticity |

Another method of determining the degree of "rejuvenation" for the present invention is to measure the diffusion coefficient of molecules across intracellular and extracellular spaces. Methods used to measure the diffusion coefficient of molecules across intracellular and extracellular spaces include the determination of the reaction time of biomolecular feed-back mechanisms based on the diffusion of molecules across a cellular, tissue and/or organ space to reach a target response element and the measurement of the diffusion rate of certain molecules across biological spaces or the diffusion rate of tracer molecules like dyes or radioisotopes. Examples of methods to determine the biomolecular feedback mechanisms include, but are not limited to, the following: (a) hypothalamic-pituitary axis: growth hormone, ACTH, TSH, or prolactin; (b) pituitary-adrenal axis: cortisol; (c) pituitary-thyroid axis: thyroxin; and (d) pituitary-gonadal axis: sex hormones, LH, and FSH. Examples of methods to determine the diffusion rate of certain molecules across biological spaces include, but are not limited to, the following: arterio-alveolar oxygen and carbon dioxide gradients; insulin resistance; and arterio-venous oxygen gradient (e.g., heart, muscle).

In one embodiment, the compounds of the present invention may be combined with a pharmacologically acceptable organ storage solution that results in a rejuvenation solution. The solution of the present invention may be utilized to rejuvenate major organs such as the kidney, heart, pancreas, liver, lungs and intestines and portions or segments thereof. In another embodiment, organs may be rejuvenated by flushing the organ after it has been removed from a cadaver with the rejuvenation solution of the present invention followed by cold storage of the organ in the rejuvenation solution at temperatures of about 4° C. Organs stored in the rejuvenation solution may then be transplanted into an appropriate transplant recipient.

For example, the rejuvenation solution of the present invention may be a pharmacologically acceptable solution such as an aqueous buffer solution containing one or more of the specific compounds claimed. In one embodiment, an aqueous phosphate buffer may be prepared, for example, by mixing sodium hydrogen phosphate ($Na_2HPO_4$) and sodium dihydrogen phosphate ($NaH_2PO_4$) in water preferably; the water should be purified by distillation, deionization, etc. prior to use. In a further example, if a cardioplegic solution for rejuvenation of hearts is desired, a phosphate buffer solution may be prepared using potassium hydrogen phosphate ($K_2HPO_4$) and/or potassium dihydrogen phosphate ($KH_2PO_4$).

In a further embodiment, the rejuvenation composition of the present invention may be adjusted to have a pH of 7.0 or greater; more particularly in the range of 7.1-7.4.

In another embodiment, the rejuvenating solutions of the present invention may contain an osmotic agent. Suitable conventional osmotic agents include any osmotic agent known for use in preservation solutions, including mannitol, sucrose, raffinose, and lactobionate. The osmotic agent is added to the rejuvenation solution in a sufficient amount to provide adequate osmolality and rejuvenation properties.

In yet another embodiment, the rejuvenating solution of the present invention may contain other components which do not adversely affect the rejuvenating properties of the solution. For example, addition of glutathione or a $C_{1-6}$alkyl glutathione monoester (M. E. Anderson et al, Arch. Biochem. Biophys., 1985, 239:538-548, ethyl ester) in amounts of about 2-10 mmol/l.

In a further embodiment, a suitable hypothermic solution, such as the solution formulated by the University of Wisconsin, that may be combined with the compositions of the present invention to rejuvenate the kidney, is composed of Sodium (30 mmol $L^{-1}$), Potassium (125 mmol $L^{-1}$), Magnesium (5 mmol $L^{-1}$), Sulphate (5 mmol $L^{-1}$), Lactobionate (100 mmol $L^{-1}$), Phosphate (25 mmol $L^{-1}$), Raffinose (30 mmol $L^{-1}$), Adenosine (5 mmol $L^{-1}$), Gluthatione (3 mmol $L^{-1}$), Allopurinol (1 mmol $L^{-1}$), Insulin (100 units $L^{-1}$), Dexamethasone (8 mg $L^{-1}$), Bactrim (0.5 ml), HES (50 g $L^{-1}$), Osmolality (320 mmol $kg^{-1}$), and pH of 7.4.

Further embodiments of suitable cold storage solutions that may be combined with the compositions of the present invention to rejuvenate the kidney comprise the Collins solution (Collins, B M, Lancet 1969;2:1219) and the Euro-Collins solution (Squifflet J P, Transplant Proc 1981;13:693). Examples of further embodiments of suitable preservation solutions that may be combined with the compositions of the present invention to rejuvenate the heart comprise the aforementioned University of Wisconsin solution, the Stanford solution (Stein D G, J Thorac Cardiovasc Surg 1991;102:657) and the St. Thomas' solution (Demertzis S, Ann Thorac Surg 1993;55:1131).

Examples of further embodiments of suitable pneumoplegia solutions that may be combined with the compositions of the present invention to rejuvenate the lung comprise the Euro-Collins and the University of Wisconsin solutions.

In a further embodiment, a suitable preservation solution that may be combined with the compositions of the present invention to rejuvenate a liver is the Euro-Collins solution. In yet a further embodiment, a suitable preservation solution that may be combined with the compositions of the present invention to rejuvenate a liver consists of the University of Wisconsin solution. Examples of further embodiments of suitable preservation solutions that may be combined with the compositions of the present invention to rejuvenate the small bowels comprise the Euro-Collins and the University of Wisconsin solutions.

Methodology for Determination of Stress vs Strain Relationship (Stiffness)

The distensibility (i.e, elasticity, rigidity, shear, tensile strength, compression, etc.) of hair, nails, tendons, etc. may be determined using widely available commercial devices, such as manufactured by Instron. Alternatively, other test methods known to a practitioner of the art may be employed.

The test assay for determining whether hair has been "rejuvenated" for the present invention is the following. Individual scalp hairs were cemented into the ends of glass capillary tubes such that several centimeters of the shaft protruded from the end. This hair was then trimmed to extend 18 mm from the end of the tube. The unit was then inserted into a micropipette positioner for study. Evaluation consisted of bending the hair by applying a specified force and displacement. Thus, this determination of stress vs strain of bending assessed elasticity, compressibility, and shear of each hair shaft. Each hair served as its own control, with baseline and post-treatment properties assessed and directly compared.

A 1 mm thick plate with a 0.5 mm diameter hole drilled through was attached to the surface of an isometric strain gauge. To perform each measurement, the capillary tube was placed over the fenestrated plate and the hair end inserted into the hole in the plate without touching the strain gauge. The hair was then straightened, if necessary, such that its axis formed a 10 degree angle with respect to vertical. Once positioned, the hair was then lowered onto the surface of the strain gauge. The force required to bend each hair a specified distance was determined over a wide range of displacements. From the stress vs strain relationships thus derived, the work to bend each hair under different treatment regimens can be directly compared. For purposes of the present invention, the term "rejuvenated" hair means an improvement of at least 20% in the measured value of the treated hair, toward the values seen in young, undamaged hair (i.e. healthy 20 year old).

To determine changes in deformability of nails treated with a rejuvenator, a nail specimen is trimmed to standard dimensions (thickness and cross sectional area) and dried for 2 hours in an oven at 45° C. The nail is then clamped within an Instron materials testing device. A stress vs strain relationship is determined using this instrument, taking care to perform testing only within the region of reversibility (i.e., not to apply excessive stress). The nail specimen is then removed from the materials testing device and exposed to a tissue rejuvenator bath at a concentration and for a time needed to provide the desired change in deformability. The nail specimen is then washed in distilled water twice for 10 minutes each and dried in an oven at 45° C. for 2 hrs. A new stress vs strain relationship is then obtained after this treatment. This shows that the strain for a specific stress is reduced by about 50%. For purposes of the present invention, the term "rejuvenated" nail means an improvement of at least 20% in the measured value of the treated nail, toward the values seen in young, undamaged nails (i.e. healthy 20 year old).

The following examples will more fully illustrate the embodiments of this invention. Therefore, they should not be construed as limiting of the remainder of the disclosure in any way. All parts, percentage and proportions referred to herein and in the appended claims are by weight unless otherwise indicated.

EXAMPLE 1

Effect of Rejuvenator on Hair Deformability

Individual hairs were prepared within capillary tubes as described above. The stress versus strain relationship was determined as a baseline. Subsequently, the hair was immersed in a solution of 3-(2-phenyl-2-oxoethyl)-4,5-dimethylthiazolium chloride (1 mM) for 15 minutes. The hair was then removed from the bath and rinsed for 5 minutes in distilled water and dried. The results are shown in FIG. 1, which illustrate that after treatment with a rejuvenator, the hair possessed increased distensibility, as indicated by the fact that for stress greater than 0.08, the resulting strain is about 50% less than that before treatment.

EXAMPLE 2

Rejuvenator Shampoo Composition

The following shampoo composition is prepared employing a compound of the present invention and is applied to hair.

| Component | Weight (%) |
|---|---|
| Sodium Lauryl Sulfate (30%) | 40.00 |
| Laurie Diethanolamide | 4.00 |

-continued

| Component | Weight (%) |
|---|---|
| 3-(2-phenyl-2-oxoethyl)-4,5-dimethylthiazolium chloride | 1.10 |
| Perfume | 0.25 |
| Dowicil 200 | 0.20 |
| Soft Water | 54.45 |

EXAMPLE 3

Rejuvenator Nail Polish Composition

The following nail polish composition is manufactured according to conventional methods containing the compounds of the present invention.

| Amount | Weight (%) |
|---|---|
| Nitrocellulose (¼" RS) | 15.00 |
| Nitrocellulose (½" RS) | 5.00 |
| Dipropylene Glycol Di-P-Aminobenzoate | 10.00 |
| Neopentyl Glycol Dioctanoate | 5.00 |
| Toluene | 47.80 |
| Ethyl Acetate | 10.00 |
| N-Methyl-2-Pyrrolidone | 2.00 |
| Isopropanol | 0.50 |
| 3-(2-phenyl-2-oxoethyl)-4,5-dimethylthiazolium chloride | 2.00 |
| Stearalkonium Hectorite | 1.00 |
| Titanium Dioxide | 0.30 |
| Black Iron Oxide | 0.30 |
| D&C Red #7 Ca Lake | 0.30 |
| D&C Red #34 Ca Lake | 0.30 |
| D&C Yellow #5 Zr Lake | 0.50 |

EXAMPLE 4

Rejuvenator Nail Composition with Antifungal

The components outlined below are mixed into a homogeneous solution which is useful for applying to finger and toe nails for rejuvenation.

| Component | Weight (%) |
|---|---|
| Alcohol SDA | 67.0 |
| Miconazole | 20.0 |
| 3-(2-phenyl-2-oxoethyl)-4,5-dimethylthiazolium chloride | 2.0 |
| Glycerin | 1.0 |
| Water | 4.0 |
| Propylene glycol | 5.0 |
| Hydroxypropyl cellulose | 1.0 |

EXAMPLE 5

Rejuvenator Hair Conditioning Composition

| Ingredient | Weight (%) |
|---|---|
| Deionized Water | 93.10 |
| Hydroxyethylcellulose | 1.35 |
| Silicone Copolymer (SF 1188 (GE)) | 0.75 |

-continued

| Ingredient | Weight (%) |
| --- | --- |
| Oleyl Alcohol | 0.75 |
| DTAC (Lauryl Trimethyl Ammonium Chloride) | 2.25 |
| 3-(2-phenyl-2-oxoethyl)-4,5-dimethylthiazolium chloride | 1.0 |
| Germaben II (preservative) | 0.50 |
| Perfume | 0.30 |

EXAMPLE 6

Tendon Rejuvenation

Figure 2:
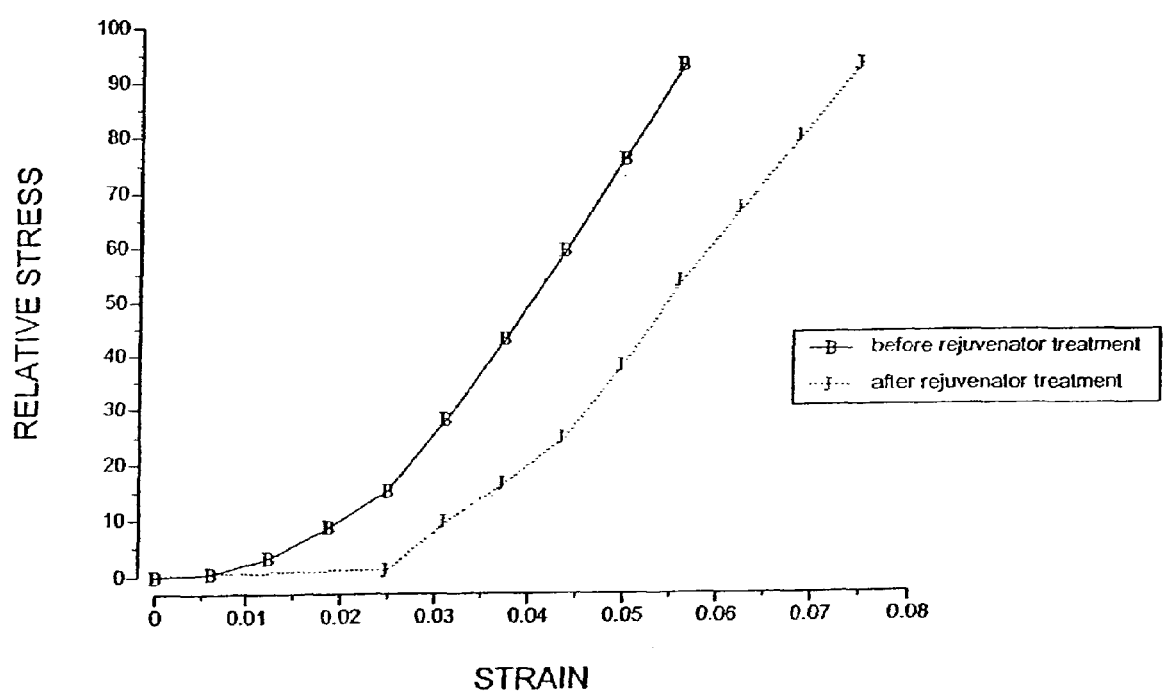
FIG. 2 shows that 3-(2-phenyl-2-oxoethyl)-4,5-dimethylthiazolium chloride, a composition of the present invention, improved the distensibility and tensile strength of a tendon after treatment.

The elasticity of the Achilles tendon of a one year old hen was determined in a materials testing device before and after ex vivo exposure to 3-(2-phenyl-2-oxoethyl)-4,5-dimethylthiazolium chloride (1 mM) in a bath for 15 minutes. The results are shown in FIG. 2. Post-treatment, distensibility was significantly increased towards that of a younger chicken. Specifically, for stress greater than 0.04, the treated tendon exhibits about 50% of the strain of the untreated tendon.

EXAMPLE 7

Tissue Diffusion Coefficient Rejuvenation

The following is an illustration of a methodology that can be used to rejuvenate ex vivo and prior to transplantation to a recipient patient the lungs removed from a donor cadaver aged 21 years or more. Older subjects exhibit a decrease in the deformability of pulmonary tissue and in the capacity of gases, including oxygen, to diffuse across alveolar membranes. Individuals' deformability and diffusion characteristics can be characterized by using the standard methodology of determination of the lung diffusing capacity for carbon monoxide (e.g., Chang et al., Chest (1992) 102:139-42). The diffusing capacity is measured in the supine patient using a single breath of carbon monoxide (0.3%) held for ten seconds using a CPI 5000 IV (Gould Instruments, Houston, Tex.), corrected for alveolar volume. A young subject (20 years old) will have approximately a 40% higher diffusion coefficient for carbon monoxide compared to older subjects (60 yrs). The ex vivo organ is flushed once with a cooled preservation solution containing 3-(2-phenyl-2-oxoethyl)-4,5-dimethylthiazolium chloride at a concentration of 0.01 to 1.0 mM. Testing in the recipient patient, following transplantation of the lungs, would show that both deformability and diffusional capacity had improved to a state comparable to the one observed in the lungs of a healthy and young individual (i.e., 20 years).

EXAMPLE 8

Rejuvenation of Organs Composition

A 70 year old male individual and established organ donor is declared brain dead 24 hours following a motor vehicle accident during which he sustained serious brain trauma. This individual has no known history of cardiovascular or pulmonary disease, infection with the hepatitis viruses, HIV or neoplastic processes. His organs are considered for donation. However, because of his age, donation of the kidneys, heart and lungs would generally not be indicated. The composition and method of the present invention are employed to rejuvenate the aged organs to a state compatible with the organs of a young individual, exhibiting deformability and diffusion characteristics of young organs. The regimen applied consists of the ex vivo perfusion of the extracted organs with an accepted preservation solution containing a sufficient concentration of the composition of the present invention for a sufficient duration of time, e.g., 15 minutes, following conventionally established guidelines for the preservation of cells, tissues and/or organs ex vivo. Thereafter, depending on need, the organs are continually perfused with a conventional preservation solution which may or may not contain additional concentrations of the compositions of the present invention.

The organ extraction as well as the ex vivo handling and implantation of the organ into the recipient are in accordance with established algorithms and procedures. Prior to implantation, the organ may be flushed with a conventional preservation solution. This flushing procedure permits the transplantation of an organ free of the compositions of the present invention.

It is believed that the transplanted organs, treated as described herein, would demonstrate improved functionality, both from a biomechanical and molecular diffusion/transportation perspective. Moreover, the tissue rejuvenation technology would also increase the number of transplantable organs significantly. There is a great demand for transplantable organs which is widely exceeding the available supply of transplantable organs. Alternatively, the technology would also improve the functionality of currently transplantable organs and improve survival and clinical outcome of such organs post transplantation.

The invention claimed is:

1. A method for the ex vivo treatment of hair or nail to improve the biomechanical and functional properties comprising externally contacting to hair or nail with an effective amount of composition comprising a compound selected from the group consisting of compounds of the formula (I):

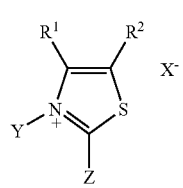

Formula (I)

wherein $R^1$ and $R^2$ are independently selected from the group consisting of hydrogen, hydroxy(lower alkyl), lower acyloxy(lower alkyl), lower alkyl, lower alkenyl, or $R^1$ and $R^2$ together with their ring carbons may be an aromatic fused ring, optionally substituted by one or more amino, halo or alkylenedioxy groups;

Z is hydrogen or an amino group;

Y is amino, or a group of the formula —$CH_2C(=O)$—R wherein R is a lower alkyl, alkoxy, hydroxy, amino or aryl group; said aryl group optionally substituted by one or more lower alkyl, lower alkoxy, halo, dialkylamino, hydroxy, nitro or alkylenedioxy groups, or a group of the formula —$CH_2R'$ wherein R' is hydrogen, or a lower alkyl, lower alkynyl, or aryl group, or a group of the formula —$CH_2C(=O)$—$N(R")R'''$ wherein (a) R" is hydrogen and R''' is a lower alkyl group optionally substituted by a $C_6$-$C_{10}$ aryl group, or a $C_6$-$C_{10}$ aryl group, said aryl groups optionally substituted by one or more lower alkyl, halo, or (lower alkoxy)carbonyl groups; or (b) R" and R''' are both lower alkyl groups; and X is a halide, tosylate, methanesulfonate, mesitylenesulfonate, or other pharmacologically acceptable anion and mixtures thereof, and a carrier therefore.

2. A method for the ex-vivo treatment of hair or nail to improve the biomechanical and functional properties comprising externally contacting the hair or nail with an effective amount of composition comprising a compound selected from the group consisting of compounds of the formula (II):

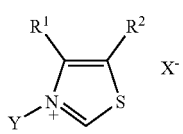

Formula (II)

wherein $R^1$ and $R^2$ are independently selected from the group consisting of hydrogen and an alkyl group optionally substituted by a hydroxy group; Y is a group of the formula —$CH_2C(\!=\!O)R$ wherein R is a heterocyclic group containing 4-10 ring members and 1-3 heteroatoms selected from the group consisting of oxygen, nitrogen and sulfur; said heterocyclic group optionally substituted by one or more substituents selected from the group consisting of alkyl, oxo, alkoxycarbonylalkyl, aryl, aralkyl groups; and said one or more substituents optionally substituted by one or more alkyl or alkoxy groups;

or a group of the formula —$CH_2C(\!=\!O)$—NHR' wherein R' is a heterocycic group containing 4-10 ring members and 1-3 heteroatoms selected from the group consisting of oxygen, nitrogen, and sulfur; said heterocyclic group optionally substituted by one or more alkoxycarbonylalkyl groups;

and X is a halide, tosylate, methanesulfonate, or mesitylenesulfonate ion, or other phaimacologically acceptable anion.

3. The method of claim 1 wherein the compound is selected from the group consisting of 3-(2-phenyl-2-oxoethyl)thiazolium, 3-(2-phenyl-2-oxoethyl)-4-methylthiazolium, 3-(2-phenyl-2-oxoethyl)-4,5-dimethylthiazolium, 3-(2-amino-2-oxoethyl)-4-methyl-5-(2-hydroxyethyl)thiazolium, 2,3-diaminothiazolium, 2,3-diamino-4,5-dimethylthiazolium, or 2,3-diamino-4-methyl-5-(2-hydroxyethyl)thiazolium.

4. The method of claim 2 wherein the compound is selected from the group consisting of 3-(2-(2-thienyl)-2-oxoethyl)-4,5-dimethylthiazolium, 3-(2-(1-pyrrolidinyl)-2oxoethyl)-4,5-dimethylthiazolium, or 3-(2-(4-morpholinyl)-2-oxoethyl-4,5-dimethylthiazolium.

5. The method of claim 1 or 2 wherein the effective amount is sufficient to treat at least one of the following: (a) damaged nails; (b) physiologically aged nails; and (c) diseased nails.

6. The method of claim 1 or 2 wherein the effective amount is sufficient to treat at least one of the following: (a) damaged hair; (b) physiologically aged hair; or (c) diseased hair.

7. The method of claim 1 or 2 wherein the effective amount is sufficient to return the biochemical and diffusional characteristics of the hair or nail to the state of a healthy 20 year old.

8. The method of claim 1 or 2 wherein the effective amount is 0.01% to 2% by weight of the composition.

9. The method of claim 6 wherein the composition is a shampoo or hair conditioning composition.

* * * * *